United States Patent [19]
Grinberg et al.

[11] Patent Number: 5,921,956
[45] Date of Patent: Jul. 13, 1999

[54] SURGICAL INSTRUMENT

[75] Inventors: Alexander Grinberg, Newton, Mass.; Graham Smith, Plaistow, N.H.

[73] Assignee: Smith & Nephew, Inc., Andover, Mass.

[21] Appl. No.: 08/937,359

[22] Filed: Sep. 24, 1997

[51] Int. Cl.$^6$ .................................................. A61M 37/00
[52] U.S. Cl. ............................ 604/95; 600/146; 600/147; 606/170
[58] Field of Search ............................... 604/95, 282, 280, 604/281, 264; 606/170; 600/146, 147, 138, 201

[56] References Cited

U.S. PATENT DOCUMENTS

| | | |
|---|---|---|
| 5,179,934 | 1/1993 | Nagayoshi et al. . |
| 5,282,821 | 2/1994 | Donahue . |
| 5,286,253 | 2/1994 | Fucci . |
| 5,322,505 | 6/1994 | Krause et al. . |
| 5,540,706 | 7/1996 | Aust et al. . |
| 5,620,447 | 4/1997 | Smith et al. . |
| 5,624,397 | 4/1997 | Snoke et al. ............................... 604/95 |
| 5,669,926 | 9/1997 | Aust et al. . |
| 5,766,196 | 6/1998 | Griffiths . |
| 5,807,241 | 9/1998 | Heimberger . |

FOREIGN PATENT DOCUMENTS

| | | |
|---|---|---|
| 0 605 763 A1 | 7/1994 | European Pat. Off. . |
| 0 623 317 A1 | 11/1994 | European Pat. Off. . |
| WO93/04634 | 3/1993 | WIPO . |
| WO94/10897 | 5/1994 | WIPO . |

*Primary Examiner*—Wynn Wood Coggins
*Assistant Examiner*—N. Kent Gring
*Attorney, Agent, or Firm*—Fish & Richardson P.C.

[57] ABSTRACT

A surgical instrument is steerable from the hub of the instrument to move a surgical tool to different offset positions. The instrument includes a shaft disposed along a longitudinal axis between a proximal region and a distal region at which the surgical tool is supported. A steering body is connected to the shaft proximally of the surgical tool and is configured to transmit proximally directed and distally directed forces applied by an actuator to a proximal end thereof to the shaft to bend the shaft in a flexible region of the shaft and offset the surgical tool from the longitudinal axis of the shaft.

26 Claims, 5 Drawing Sheets

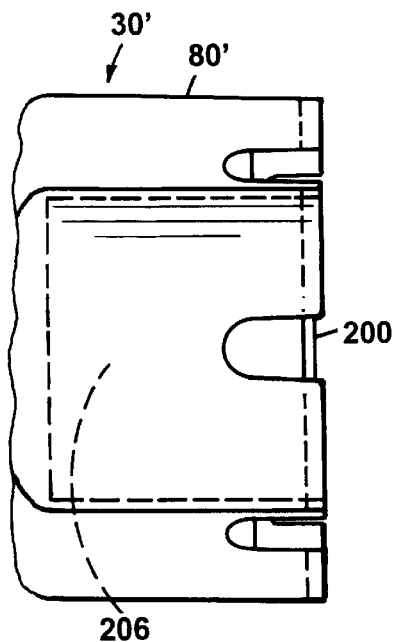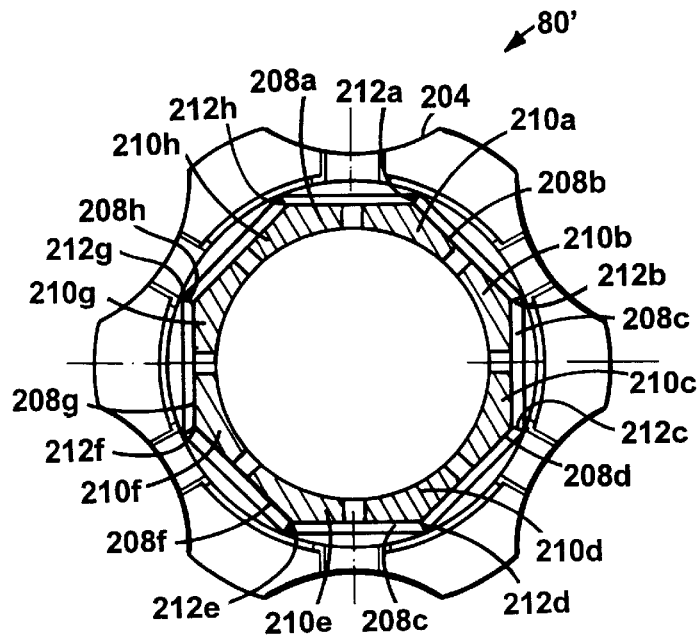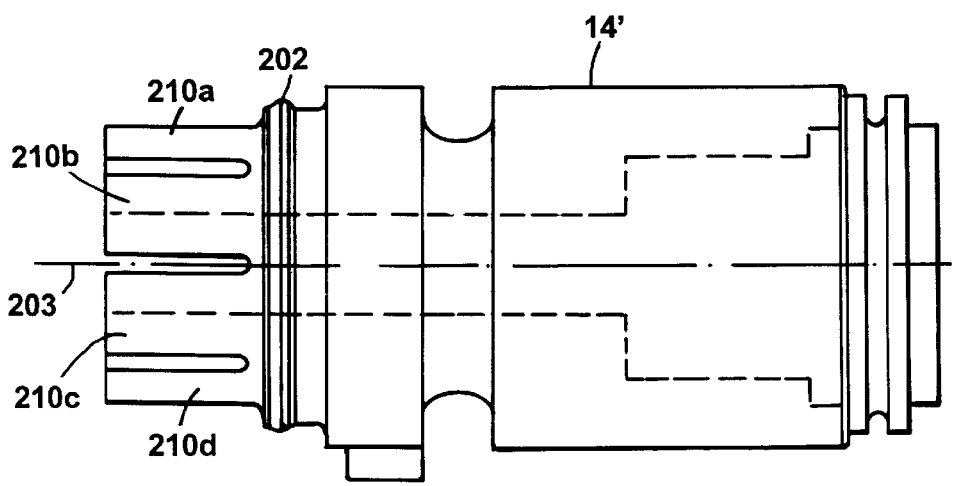

SURGICAL INSTRUMENT

BACKGROUND

This invention relates to surgical instruments for removing soft or hard tissue from a body. In particular, the invention relates to endoscopic surgical instruments, including those for use in arthroscopy.

Endoscopic surgical instruments typically include an outer tubular shaft that extends from a hub and receives an inner tubular shaft which is rotated or otherwise moved by a motor. A cutting implement such as a blade or burr attached to the distal end of the inner shaft is exposed to tissue through an opening in the distal end of the outer shaft. Tissue severed by the cutting implement and irrigating fluid present at the surgical site are drawn into the interior of the inner shaft by suction for withdrawal from the body.

Some endoscopic surgical instruments are straight; in other, curved instruments, the outer shaft is bent between its proximal and distal ends to offset the cutting implement with respect to the longitudinal axis of the instrument. The inner shaft is flexible within the bend region allow it to transmit force through the curve and operate the cutting implement. The outer shaft of many curved surgical instruments is rigid, and thus imposes a fixed direction and amount of curvature. Alternatively, the outer shaft may be flexible so that the user can impose variable curvatures by grasping the hub and outer shaft and bending the outer shaft by a selected amount.

SUMMARY

This invention features a surgical instrument in which the surgical tool is steerable to different offset positions from the hub of the instrument. This eliminates the need for the user to grasp and bend the outer tube. Thus, the surgical tool can be easily and accurately steered to different positions without removing the instrument from the surgical site.

In one general aspect, the surgical instrument includes a steering body connected to the shaft proximally of the surgical tool and configured to transmit proximally directed and distally directed forces applied by an actuator to a proximal end thereof to the shaft to bend the shaft in a flexible region and offset the surgical tool from the longitudinal axis of the shaft. Another aspect of the invention features a method for operating the instrument.

Preferred embodiments may include some or all of the following features.

The steering body comprises a plurality of generally rigid members disposed along the shaft. Each member has a distal end connected to the shaft proximally of the surgical tool, and a flexible region disposed axially adjacent to the flexible region of the shaft. The actuator is coupled to a proximal end of each member for selectively moving the members in opposite proximal and distal directions along the axis, thereby to transmit the proximally directed and distally directed forces to the shaft. The members are connected to the shaft between the shaft's flexible region and a tissue-admitting opening in the shaft. Preferably, the members are semi-cylindrical sleeves which enclose the shaft.

The members are each relieved with a plurality of openings, such as circumferentially extending slots disposed therein transversely to the axis, to provide their flexible regions. Preferably, the slots are arranged to define a continuous strip of material that extends along a substantially straight line over an entire length of the flexible region of each member.

The instrument includes a hub disposed at the proximal region of the shaft, and the actuator includes a knob mounted for relative rotation on the hub. The proximal ends of the members are linked to the knob by a transversely extending pins which engage within a plurality of channels in the knob. The channels are oriented with respect to the axis so that the engagement of the pins with the channels causes the members to move in opposite proximal and distal directions along the axis in response to relative rotation between said knob and said hub. This opposing "push-pull" motion transmits the proximally directed and distally directed forces to the shaft and steers the surgical tool. The channels are oriented in opposite inclined directions with respect to the longitudinal axis and are preferably helical.

To avoid twisting of the proximal ends of the members in response to the torque imposed by the knob, the members are equipped with second transversely extending pins which are disposed proximal of the first-mentioned pins and received in a plurality of passages in the hub. The passages are oriented along the longitudinal axis so that the engagement of the second pins with the passages limits rotation of the proximal ends of the members in response to relative rotation between the knob and the hub.

In one embodiment, the knob is mounted to the hub to allow continuous relative rotation therebetween. Alternatively, the mounting permits relative rotation in discrete steps.

The instrument also includes an inner shaft movably disposed within the outer shaft and having a flexible region positioned axially adjacent to the flexible region of the outer shaft. The surgical tool comprises an opening in the distal region of the outer shaft and an implement (e.g., a sharpened edge at the distal end of the inner shaft) carried by the inner shaft for cutting tissue exposed thereto through the opening.

Preferably, the inner shaft is relieved with a plurality of openings to provide its flexible region, and a sheath may be disposed over at least this flexible region. A sheath is also placed over the steering members between their distal ends and the hub. The sheaths help prevent leakage of suction (applied, as discussed above, to remove severed tissue fragments from the surgical site) through the relieved flexible regions.

Among other advantages, because the surgical tool is steered while the instrument remains in situ, surgery need not be interrupted to withdraw the instrument, bend it, and reinsert it in the body. In addition, the trauma associated with removing and reinserting the instrument is avoided. The push-pull action more easily and accurately steers the surgical tool than if the bending force was applied in one direction only (e.g., such as by pulling the tip proximally), thereby lessening fatigue.

Other features and advantages of the invention will be apparent from the following detailed description and claims.

DRAWINGS

Figure 3:
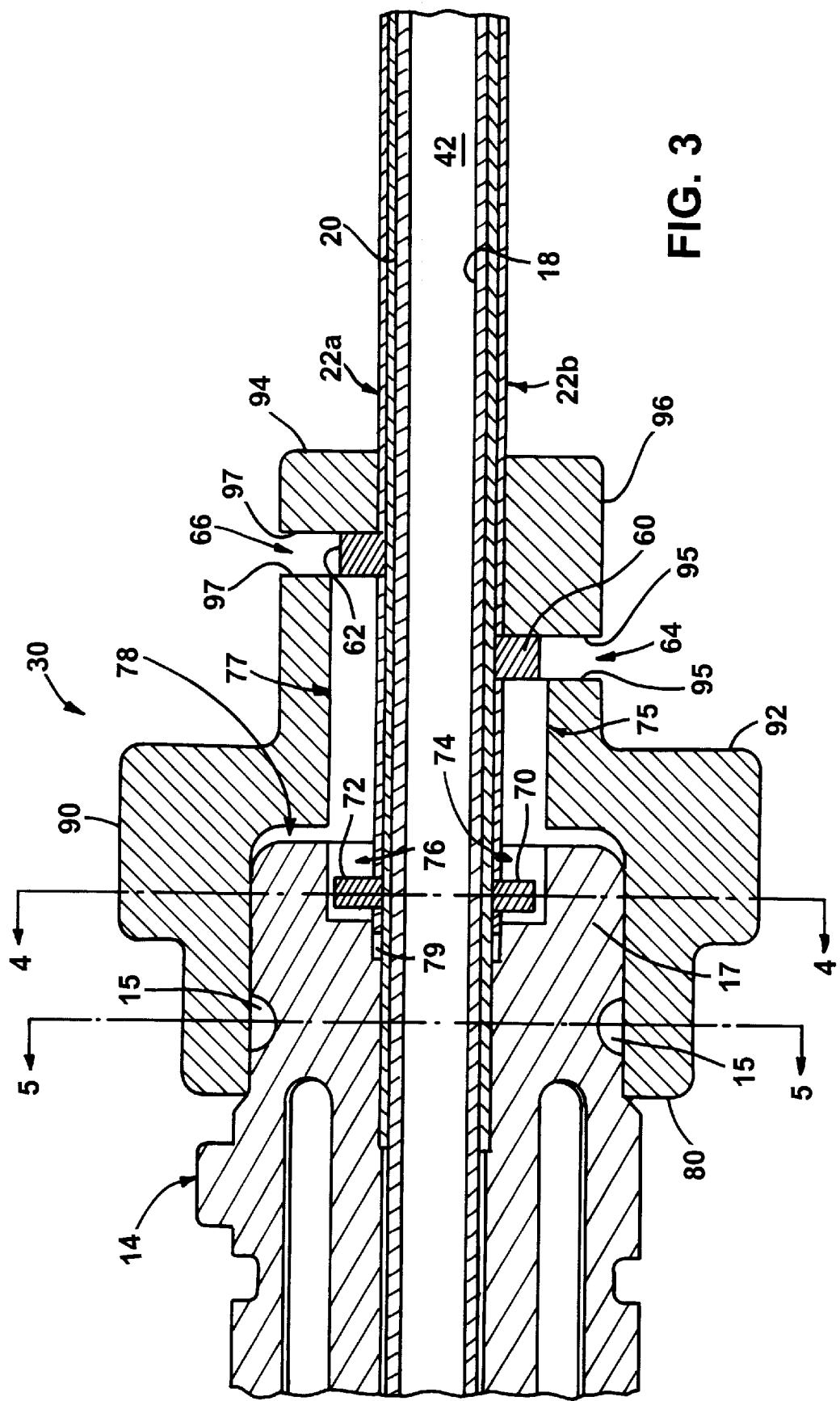
FIG. 3 is an enlarged, cross-sectional side view of the steering mechanism of the instrument of FIG. 1.
Figure 4:
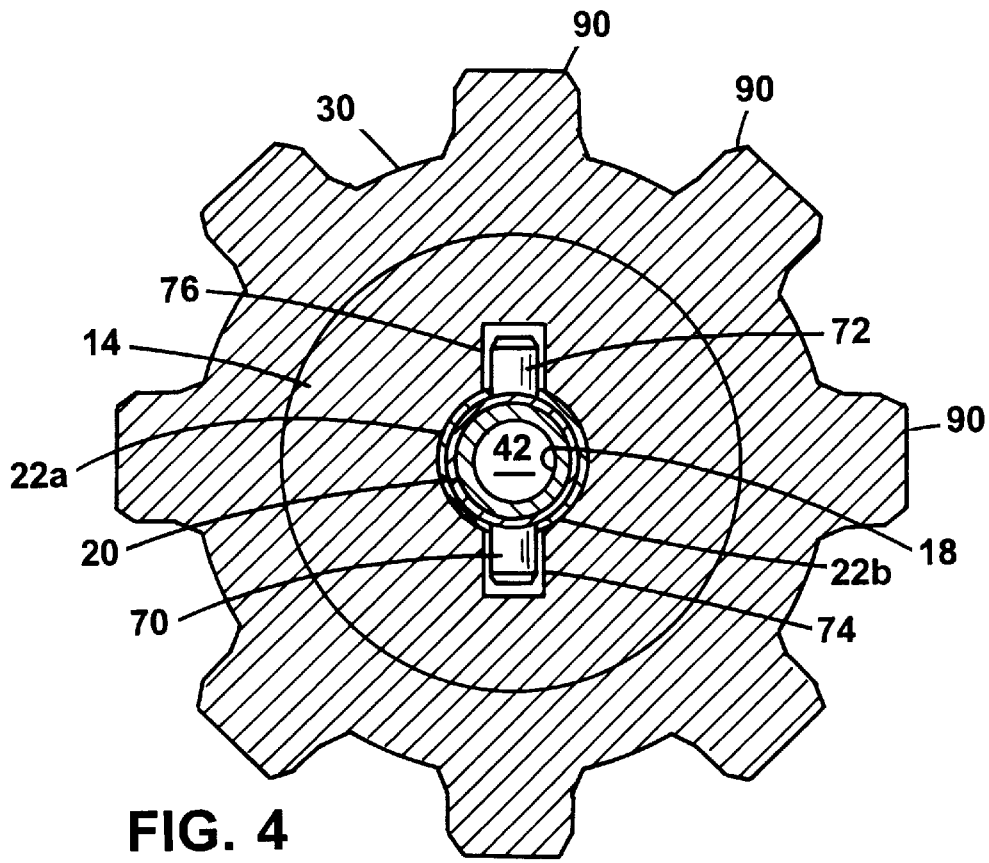
Figure 5:
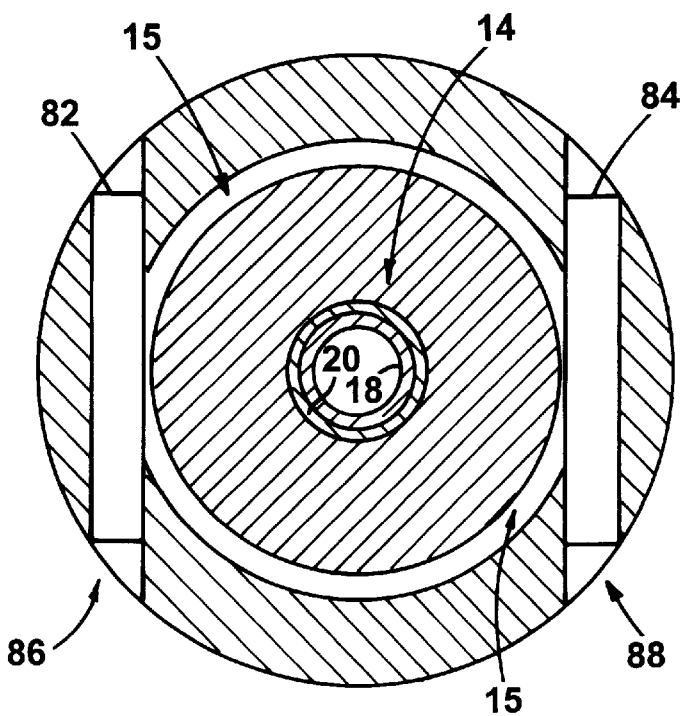

FIGS. 4 and 5 are cross-sectional views of the steering mechanism, taken along line 4—4 and line 5—5, respectively, of FIG. 3.

Figure 6:
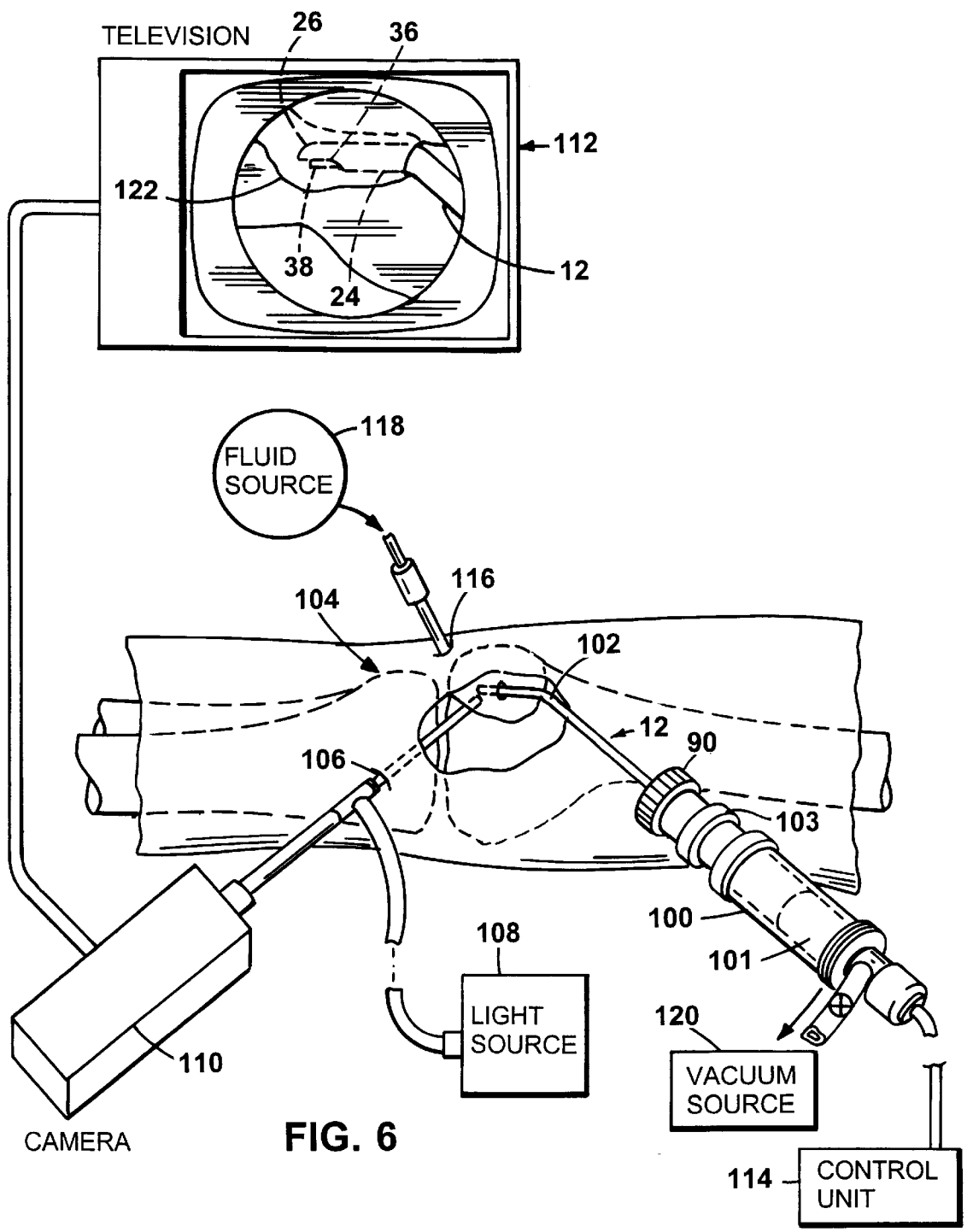

FIG. 6 shows the instrument in use during a surgical procedure.

FIGS. 7–9 show an alternative embodiment of the steering mechanism.

Like numerals refer to like elements in the drawings.

DESCRIPTION

Figure 1:
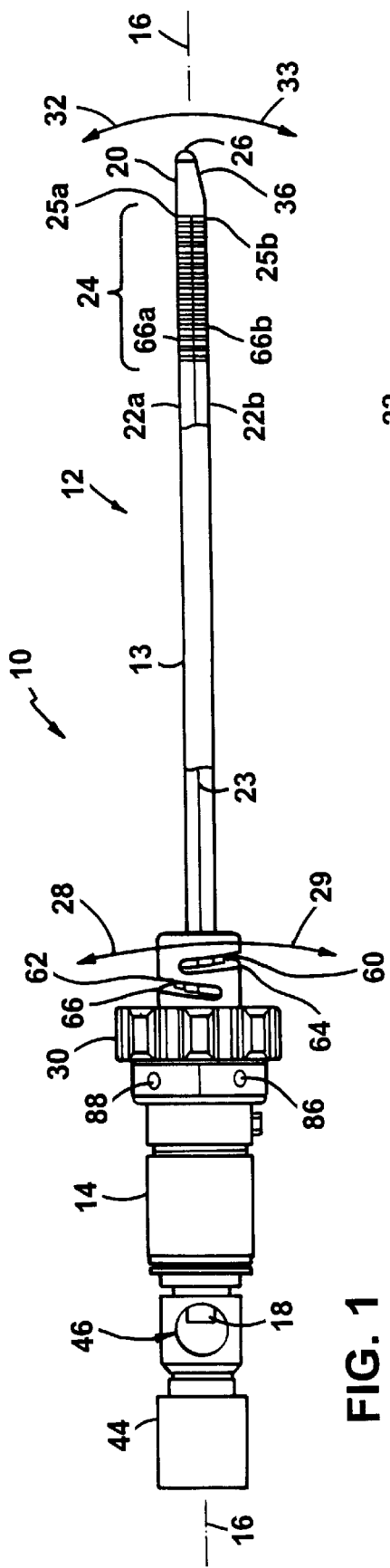
FIG. 1 shows a steerable surgical instrument.
Figure 2:
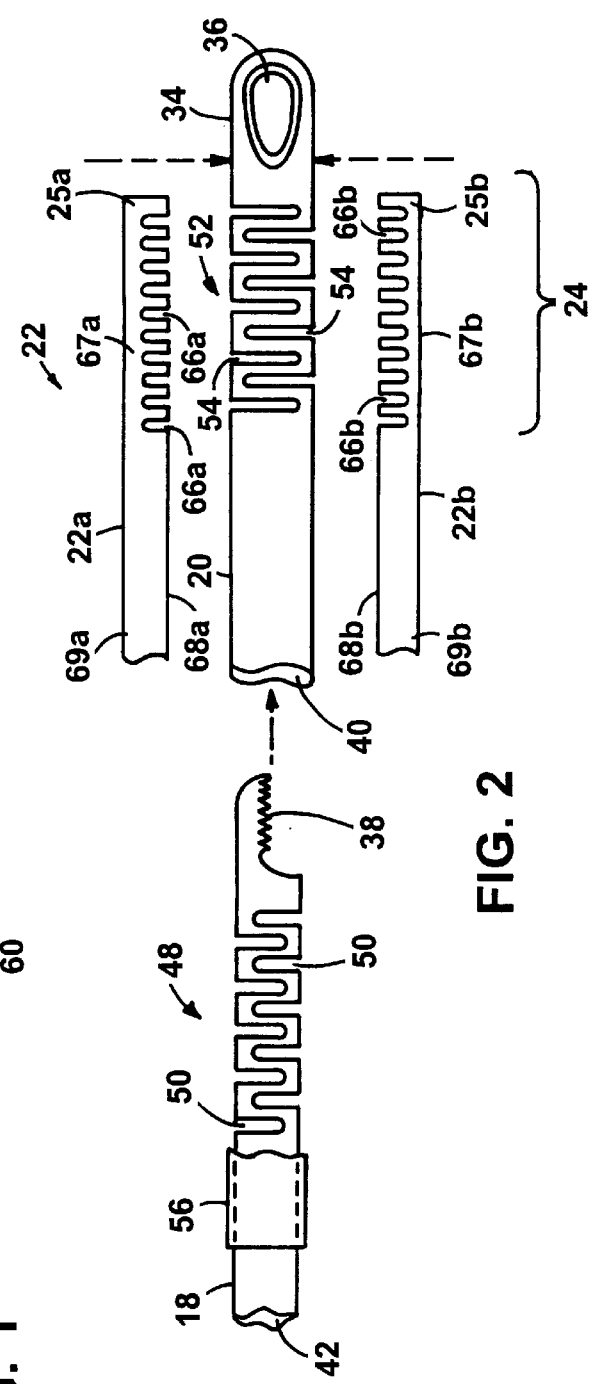
FIG. 2 is an exploded view of some of the components of the instrument of FIG. 1.

Referring to FIGS. 1 and 2, surgical instrument 10 includes a cutting assembly 12 which extends distally from a hub 14 along a longitudinal axis 16. Cutting assembly 12 includes an inner tubular shaft 18 which is rotatably received within an outer tubular shaft 20, which is in turn enclosed over much of its length by a steering sleeve 22. Shafts 18, 20 and sleeve 22 are generally rigid but are flexible in a bend region 24 (FIG. 1). Sleeve 22 comprises a pair of semi-cylindrical sleeve halves 22a, 22b having proximal ends linked to a rotatable knob 30 on hub 14, and distal ends attached to the exterior surface of shaft 20 proximally of the distal tip 26 of cutting assembly 12.

The linkage of sleeve 22 to knob 30 is discussed in more detail below. Functionally, however, when knob 30 is rotated in either a clockwise direction (shown by arrow 28) or a counterclockwise direction (shown by arrow 29) it applies opposite proximally directed and distally directed axial forces to sleeve halves 22a, 22b to move sleeve halves 22a, 22b axially in opposite proximal and distal directions along shaft 20. The axial motion of sleeve halves 22a, 22b exerts a "push-pull" force on distal tip 26, thereby bending shafts 18, 20 and sleeve 22 in flexible region 24 and steering distal tip 26 in corresponding side-to-side directions (shown by arrows 32, 33, respectively) with respect to longitudinal axis 16. Thus, by rotating knob 30, the user can adjust the direction of cutting performed by instrument 10 over a wide lateral range (such as 30 degrees) during a surgical procedure, while keeping instrument 10 in situ.

Tubular shafts 18, 20 and sleeve 22 are metal (e.g., stainless steel), while hub 14 and knob 30 are plastic. With this construction, instrument 10 is economically disposable after a single use (although the instrument may be sterilized, such as by autoclaving, and reused, if desired). The proximal end of tubular shaft 20 is received within and rigidly mounted to hub 14. The distal end 34 of shaft 20 includes an opening 36 with sharpened edges which defines a tissue cutting window. Corresponding sharpened edges 38 of an opening at the distal end of inner tubular shaft 18 cut tissue admitted through opening 36 as shaft 18 is rotated within a bore 40 in shaft 20. Thus, together, the edges of opening 36 and inner shaft edges 38 define a surgical tool for instrument 10. Edges 38 are serrated, but may be straight instead, and other surgical tool configurations (e.g., abrading burrs) may alternatively be employed.

The proximal end of inner shaft 18 extends through hub 14 and is secured to a plastic shank 44 that is rotatably received by hub 14. Hub 14 and shank 44 are configured to be received within a motorized handpiece (FIG. 6) which engages shank 44 to rotate inner shaft 14 within shaft 20 so that edges 38 cut tissue admitted through opening 36. Severed tissue fragments are aspirated through an interior suction bore 42 in inner shaft 18 by suction applied at the handpiece and are conveyed to drainage via an exit portal 46 in shank 44. An example of a handpiece suitable for use with instrument 10 is described in commonly assigned U.S. Pat. No. 4,705,038, which is incorporated herein by reference (the "'038 patent").

Inner tubular shaft 18 is relieved in a region 48 slightly proximal of its distal tip with a series of axially spaced, circumferential slots 50 to render region 48 flexible. Similarly, a region 52 of outer tubular shaft 20 located slightly proximally of distal end 34 is relieved with a series of axially spaced, circumferential slots 54 so that region 52 is flexible. Regions 48, 52 are axially aligned when inner shaft 18 is in place within outer shaft 20. Slots 50, 54 can be formed in any suitable way and configured in any suitable pattern. Examples are found in U.S. Pat. No. 5,322,505, assigned to the present assignee and incorporated herein by reference (the "'505 patent"). Preferably, each series of slots 50, 54 is arranged so that adjacent slots extend into respective shafts 18, 20 in opposite directions, as shown in FIG. 2. Slots 50 may be covered by a layer 56 of, e.g., heat shrink plastic (shown cut away in FIG. 2 so that the slots can be seen) to avoid interference with the edges of slots 54 as shaft 18 rotates. Layer 56 should be sufficiently thin (e.g., 0.001 inches) to avoid binding without urging cutting edges 38 away from the edges of opening 36. Examples of materials suitable for use as sheath 56 include polymers such as polyester, polyurethane and TEFLON®.

Semi-cylindrical sleeve halves 22a, 22a enclose and are supported in opposing, sliding contact by outer shaft 20, and meet each other at a pair of seams 23 (only one of which is shown in FIG. 1). A pair of transversely extending pins 60, 62 attached to sleeve halves 22a, 22b, respectively, near their proximal ends are received by corresponding helical channels 64, 66 in knob 30, as discussed in more detail below. The distal ends 25a, 25b of sleeve halves 22a, 22b are secured (such as by spot welding) to the exterior surface of outer tubular shaft 20 between flexible region 52 and outer shaft opening 36.

Sleeve halves 22a, 22b are relieved with a series of axially-spaced, circumferential slots 66a, 66b, respectively, slightly proximally of distal ends 25a, 25b. When sleeve halves 22a, 22b are in place on outer shaft 20, slots 66a, 66b are disposed in opposing relationship in flexible region 24 overlying slots 50, 52 of inner and outer shafts 18, 20. Slots 66a, 66b are formed in the same manner as slots 50, 52 (e.g., by electric discharge machining). Each series of slots 66a, 66b extends in a single direction from the planar side 68a, 68b of the respective sleeve half. Thus, a continuous, axially directed flexible strip of material 67a, 67b is defined between the ends of the individual slots 66a, 66b of each series. Flexible strips 67a, 67b connect the rigid proximal regions 69a, 69b of sleeve halves 22a, 22b with distal ends 25a, 25b, and extend along a substantially straight line over the entire lengths of the flexible regions of sleeve halves 22a, 22b.

The orientation of flexible strips 67a, 67b, on shaft 20 defines a plane in which the surgical tool is steered from side to side by rotating knob 30. More specifically, with strips 67a, 67b are arranged as shown in FIG. 1, sleeve halves 22a, 22b (and hence shafts 18, 20) will bend up and down with respect to opening 36 (i.e., in the direction of arrows 32, 33). In contrast, if sleeve halves 22a, 22b are arranged as shown in FIG. 2—with flexible strips 67a, 67b positioned on either side of opening 36—the bend direction will be laterally with respect to opening 36. The arrangement of slots 50, 54 on inner and outer shafts 18, 20 is preferably selected to allow easy bending in the directions defined by sleeve halves 22a, 22b.

The length of flexible region 24 is a function of lengths of flexible regions 48, 52 of shafts 18, 20 and the length of the flexible region of sleeve halves 22a, 22b. In this embodiment, the flexible region of sleeve halves 22a, 22b is approximately one inch long, and is slightly longer than that of flexible regions 48, 52, but any suitable dimensions may be used. It will be appreciated that the amount by which distal tip 26 can be moved from side to side is a function of the length of flexible region 24.

FIGS. 3–5 illustrate the connection between hub 14 and knob 30, and the linkage between knob 30 and the proximal ends of sleeve halves 22a, 22b. As discussed above, a pair of pins 60, 62 are mounted to, and protrude radially from, respective sleeve halves 22a, 22b near the proximal ends thereof for engagement within helical channels 64, 66. A pair of radially extending, secondary pins 70, 72 are secured to sleeve halves 22a, 22b, respectively, proximally of pins 60, 62. Pins 60, 62 and secondary pins 70, 72 are secured to sleeve halves 22a, 22b in any suitable way, such as by being press fit or welded within holes (not shown) in the sleeve halves. In addition, pins 60, 62 and studs 70, 72 may be coated with any suitable low friction material for smooth operation, as discussed below.

Secondary pins 70, 72 are (but need not be) circumferentially aligned with pins 60, 62 and are received within a corresponding pair of axially oriented, open-ended passages 74, 76 formed in the distal end 17 of hub 14 (FIG. 4). As shown in FIG. 4, passages 74, 76 are only slightly wider than secondary pins 70, 72 for purposes which will become apparent. A corresponding pair of grooves 75, 77, respectively, are formed in knob 30 for assembly purposes. Grooves 75, 77 extend from open proximal ends which communicate with a cavity 78 in a cylindrical proximal section 80 of knob 30, to open distal ends which communicate with respective helical channels 64, 66 in a distal section 94 of knob 30.

Hub 14 is similar to the hub described in the '505 patent but differs from it in some respects. One is the inclusion of passages 74, 76 discussed above. In addition, hub 14 includes an annular groove 15 (FIGS. 3 and 5) in its exterior surface near distal end 17. Knob 30 is rotatably mounted on the distal end of hub 14 by a pair of cylindrical posts 82, 84 which are press fit into respective through holes 86, 88 in knob proximal section 80 and positioned longitudinally within groove 15. Posts 82, 84 may also be coated with a low-friction material for smooth rotation. When in place within through holes 86, 88, posts 82, 84 lock knob 30 onto hub 14 while permitting knob 30 to be rotated with respect to hub 14. The exterior surface of knob proximal section 80 includes a series of raised, circumferentially spaced ridges 90 which are easily grasped by the user to rotate knob 30.

Helical channels 64, 66 are formed in the axially extending walls 96 of knob distal section 94. Distal section 94 has a reduced diameter relative to proximal section 80 and meets proximal section 80 at an annular shoulder 92. Helical channels 64, 66 are oriented at opposite oblique angles (e.g., ±15 degrees) with respect to longitudinal axis 16 (FIG. 1) to define oppositely-inclined camming sidewalls 95, 97 for pins 60, 62. Distal section 94 extends axially for a length sufficient to accommodate helical channels 64, 66, which extend nearly completely around the circumference of distal section 94. The helix angle of channels 64, 66 is one factor that determines the amount of bending produced by knob 30, and can be increased or decreased to produce greater, or lesser, bending amounts.

Sleeve halves 22a, 22b and knob 30 are assembled onto hub 14 and outer tubular shaft 20 of instrument 10 as follows. First, with shaft 20 held in a fixture (not shown), distal ends 25a, 25b of sleeve halves 22a, 22b are welded to the exterior surface of shaft 20, between flexible region 52 and opening 36. The proximal end of shaft 20 is then inserted into hub distal end 17 so that secondary pins 70, 72 at proximal ends of sleeve halves 22a, 22b are received within passages 74, 76 in hub distal end 17. An annular groove 79 in distal end 17 communicates with the proximal ends of passages 74, 76 and receives the proximal tips of sleeve halves 22a, 22b to allow secondary pins 70, 72 to be inserted fully proximally into passages 74, 76. Shaft 20 is secured to hub 14 in any suitable way.

Next, knob 30 is inserted over distal end 34 of outer shaft 20 and advanced to hub 14. Knob 30 is positioned so that grooves 75, 77 are aligned with pins 60, 62 on sleeve halves 22a, 22b, and is then slid proximally onto hub 14. As a result, pins 60, 62 enter the open proximal ends of grooves 75, 77 and pass into channels 64, 66 as hub distal end 17 is fully inserted into chamber 78. Channels 64, 66 are arranged on knob 30 so that when knob 30 is fully seated on hub 14, pins 60, 62 are located in channels 64, 66 at approximately their midpoints.

Knob 30 is positioned on hub 14 so that holes 86, 88 (FIG. 5) are axially aligned with groove 15. Then, posts 82, 84 are driven through holes 86, 88 and into engagement within groove 15 to secure knob 30 on hub 14. With knob 30 secured in place, pins 60, 62 are engaged within channels 64, 66, and secondary pins 70, 72 are received within hub axial passages 74, 76.

Inner tubular shaft 18 is inserted through hub 14 until cutting edges 38 are placed at the distal end 36 of outer shaft 20 and shank 44 is seated within hub 14. Of course, inner shaft 18 may be installed prior to attaching sleeve halves 22a, 22b and knob 30 to outer shaft 20 and hub 14. In either case, assembly is completed by installing a plastic sheath 13 (FIG. 1) over sleeve halves 22a, 22b. Sheath 13 (which is cut away in FIG. 1 to expose the majority of the length of sleeve halves 22a, 22b) extends from knob 30 to sleeve distal ends 25a, 25b and is preferably formed from a heat shrink plastic material, such as those discussed above for sheath 56. Sheath 13 need not extend all the way to knob 30.

During use of surgical instrument 10 in a surgical procedure, the user rotates knob 30 with respect to hub 14 to selectively steer the distal tip 26 of cutting assembly 12 (and hence the surgical tool defined by cutting edges 38 and outer shaft window 36) from side to side with respect to axis 16. When knob 30 is rotated in either the clockwise or counterclockwise direction on hub 14, pins 60, 62 travel in sliding contact with sidewalls 95, 97 of respective channels 64, 66, thereby translating the rotational motion of knob 30 into axial motion of sleeve halves 22a, 22b in opposite directions with respect to shaft 20. The engagement of secondary pins 70, 72 within axially extending passages 74, 76 of stationary hub 14 allows sleeve halves 22a, 22b to travel axially past each other along seam 23, while preventing the proximal ends of sleeve halves 22a, 22b from rotating around shaft 20 in response to the torque applied by knob 30. Accordingly, the rotation of knob 30 is translated into a smooth "push-pull" motion of sleeve halves 22a, 22b along shaft 20 without twisting of the proximal ends of the sleeve halves. The low friction coatings applied to pins 60, 62, secondary pins 70, 72, and posts 82, 84 enhance the ease with which knob 30 is rotated on hub 14.

More specifically, when knob 30 is rotated in a clockwise direction (in the direction of arrow 28, FIG. 1), the sliding engagement of pin 60 in helical channel 64 exerts a distally directed (i.e., a "pushing") force on sleeve half 22b. In contrast, the engagement of pin 62 in helical channel 66 exerts a proximally directed (i.e., a "pulling") force on sleeve half 22a. Because the distal ends 25a, 25b of sleeve halves 22a, 22b are anchored to shaft 20 and sleeve 22 and shafts 18, 20 are flexible in region 24, the push-pull force applied by sleeve halves 22a, 22b cooperate to cause shafts 18, 20 to bend in flexible regions 48, 52 to one side of axis 16 (i.e., in the direction of arrow 32, FIG. 1).

Flexible strips 67a, 67b of sleeve halves 22a, 22b are sufficiently axially stiff to bend distal end 26 while also being sufficiently flexible (due to the presence of slots 66a, 66b) to resiliently accept the resulting curvature in bend region 24 without crimping. The resilience of strips 67a, 67b tends to urge knob 30, and hence sleeves 22a, 22b into a "neutral" position in which distal tip 26 is positioned on longitudinal axis 16.

The amount by which the distal tip 26 of cutting assembly 12 is bent is a function of the amount by which knob 30 is rotated. When knob 30 is rotated to its full clockwise position (i.e., so that pins 60, 62 engage the ends of channels 64, 66), distal tip 26 is offset by between approximately 15 degrees and 20 degrees from axis 16. The bend amount can be varied by adjusting such parameters as the helical angle of channels 64, 66 and the length of flexible region 24.

When knob 30 is rotated in the opposite, counterclockwise direction (i.e., in the direction of arrow 29, FIG. 1), the axially-directed forces applied to sleeve halves 22a, 22b are reversed. That is, the engagement of pin 60 in channel 64 imparts a "pulling" force on sleeve 22b, and a "pushing" force is exerted on sleeve 22a by the engagement of pin 62 in channel 66. As a result, distal tip 26 is steered to the opposite side of axis 16 (i.e., along arrow 29 in FIG. 1) by an amount that corresponds to the amount of rotation applied to knob 30.

Thus, it will be appreciated that instrument 10 allows the user to steer distal tip 26 of cutting assembly 12 over a continuous range of angular positions between opposite side-to-side extremes defined by the limits of rotation of knob 30.

FIG. 6 illustrates an exemplary surgical procedure in which instrument 10 can be used. Hub 14 of surgical instrument 10 is inserted onto the distal end of a motorized handpiece 100 until shank 44 (FIG. 1) is engaged by the drive shaft of motor 101. With hub 14 fully inserted, knob 30 is positioned adjacent the distal end 103 of handpiece 100, and thus is readily accessible by the same hand that the surgeon uses to hold handpiece 100. Accordingly, the surgeon can easily steer distal tip 26 while he or she manipulates handpiece 100.

During the surgical procedure, cutting assembly 12 is introduced through a puncture wound 102 into the knee joint 104, below the patella. Light is projected into the joint via a second puncture 106 using a fiber optic light source 108, and a visual image of the surgical site is returned through a separate optical path to a television camera 110. The image is delivered by camera 110 onto a television screen 112 for viewing by the surgeon. (Alternatively, the surgeon can view the image using an eyepiece, or the image can be recorded.)

The operation (e.g., speed, torque, direction of rotation) of motor 101 is controlled by a control unit 114 and other operational controls (such as a footswitch unit or handpiece switches, not shown). Motor 101 is capable of rotating inner tubular shaft 18 over a wide range of speeds, e.g., between about 100 rpm and 5000 rpm, and can deliver a torque of up to 25 oz. inches. Different types of surgical instruments such as instrument 10 have rotational and torsional limits. To prevent the surgeon from inadvertently operating instrument 10 at dangerously high speeds and torques, instrument 10 identifies to sensors in handpiece 100 what type of instrument it is, and the speed of and torsion applied by motor 101 is controlled so that these limits are not exceeded. (This control technique is described in the '038 patent.)

During the surgical procedure, the body joint is inflated with fluid introduced through a third puncture wound 116 from a fluid source 118. The fluid irrigates the site and renders the tissue in the joint mobile so that it floats and can be displaced (similar to the movement of seaweed in water).

The surgeon progressively cuts away the synovial tissue by moving instrument 10 from side to side and in the axial direction (while viewing television screen 112). Tissue fragments cut by instrument 10 are withdrawn from the surgical site along with irrigation fluid via bore 42 (FIG. 2) in response to suction applied by vacuum source 120. Sheath 13 (FIG. 1) together with sheath 56 (FIG. 2) help prevent vacuum leakage. In addition, sheath 13 avoids tissue at the surgical site becoming lodged in slots 66a, 66b of sleeve 22.

It will be appreciated that, with instrument 10 in the position shown FIG. 6, the surgeon has rotated knob 30 sufficiently to steer opening 36 and cutting edges 38 to the side of axis 16 and against tissue 122 to be cut. Accordingly, inner and outer shafts 18, 20 and sleeve 22 are bent in flexible region 24. The rotation of motor 101 and the torsion that it provides are efficiently delivered by inner shaft 18 to the cutting implement (i.e., cutting edges 38) through flexible region 48 (FIG. 2). Although region 48 is sufficiently flexible to accept the curvature imposed by the push-pull action of sleeve 22, it has a high degree of torsional stiffness and thus provides good torque response. That is, torsion applied by motor 101 is transmitted to cutting edges 38 substantially immediately when inner shaft 18 is rotated from its rest position, without requiring any significant "preloading" of flexible region 48 prior to passing the torque to distal end 26. Also, flexible region 48 does not expand in diameter by any significant amount as it rotates and applies torque to cutting edges 38, reducing the possibility that inner shaft 18 will bind within outer shaft 20 during rotation. This risk is further reduced by the presence of heat shrink plastic layer 56 (FIG. 2).

If the surgeon wishes to change the angle of attack of cutting edges 38 during the procedure, he can steer distal tip 26 from the position shown in FIG. 6 to another angular position with respect to longitudinal axis 16 by rotating knob 30 with the hand used to grasp handpiece 100. There is no need to remove cutting assembly 12 from the body to change the steered direction of tip 26, and thus surgery may proceed uninterrupted while the surgeon steers distal tip 26 to another tissue cutting position. Thus, not only is the procedure simplified for the surgeon, trauma to the patient from multiple insertions of the surgical instrument is also reduced. Moreover, the surgeon can observe the repositioning of tip 26 on display 112 as he rotates knob 30 to ensure that tip 26 is accurately repositioned.

Other embodiments are within the scope of the following claims.

For example, although the slot configurations of inner and outer shafts 18, 20 are preferably identical, different slot patterns may be used to further reduce the risk of inner shaft 18 binding as it rotates within outer shaft 20. Shafts 18, 20 and sleeve 22 may be rendered flexible in other ways, for example, with non-slotted openings (such as round holes). Alternatively, any of the flexible regions of shafts 18, 20 and sleeve 22 may be composed of other structures, such as the counter-wound helical coils described in U.S. Pat. No. 4,646,738, issued to Trott, which is incorporated herein by reference.

Inner shaft 18 may move in other ways within outer shaft 20 (e.g., axially).

Sleeve 22 may be made from a flexible, non-metal material, and may be a unitary structure (such as a plastic sleeve), as long as sleeve 22 remains sufficiently axially stiff to exert the push-pull steering forces while also being bendable to accommodate the resulting curvature of shafts 18, 20. The distal end of sleeve 22 may be secured to outer shaft 20 in ways other than by welding.

Shafts 18, 20 may also be plastic and be, e.g., equipped with metal distal ends to provide suitable cutting implements.

Knob 30 may be rotatably attached to hub 14 in other ways, such as by a snap-fit connection.

A friction engagement with hub 14 may be provided to retain knob 30 in any rotational position set by the user. This would somewhat counteract the resiliency of flexible strips 76*a*, 67*b* and allow the user to release knob 30 and still maintain cutting assembly 12 in the steered position.

The knob may be mounted to the hub to allow ratchet-like rotation, that is, so that their relative rotational positions are adjustable in discrete steps, rather than continuously.

FIGS. 7–9 show an example of a ratcheting connection between a knob and a hub from U.S. Pat. No. 5,620,447, which is assigned to the present assignee and incorporated herein by reference. In the arrangement shown in FIGS. 7–9, the relative rotational positions of the knob and hub are changed in 45 degree increments. It will be appreciated that smaller increments may be preferred for steering surgical instrument 10.

The proximal section 80' of ratcheting knob 30' is shown in FIGS. 7 and 8 (the distal section of the knob is identical to that discussed above and is not shown). A shoulder 200 on the inner surface of the proximal end of knob section 80' engages a mating shoulder 202 on the outer surface of the distal end of hub 14' (FIG. 9), such that knob 30' rotatably mounts to hub 14'. Knob 30' is provided with a series of circumferentially spaced indentations 204 and ridges that facilitate the user's efforts manually to manipulate knob 30'. A central chamber 206 in knob section 80' receives the distal end of hub 14'.

The interior of knob proximal section 80' is octagonal in cross-section, its inner surface being composed of eight flat surfaces 208*a–h* of equal width. Cantilevered from the distal end of hub 14' are eight distally projecting flexible fingers 210*a–h* spaced by equal amounts (e.g., 45°) around the circumference of shoulder 202. Fingers 210*a–h* lie perpendicular to the longitudinal axis 203 of the instrument. Each of fingers 210*a–h* is an irregular pentagon in cross-section, such that when knob section 80' is assembled onto hub 14', the radial outermost point 212*a–h* of each finger 210*a–h* rests in an apex formed by the intersection of adjacent flat surfaces 208*a–h*.

Fingers 210*a–h* and flat surfaces 208*a–h* coact to allow the relative rotational orientation between knob 30' and hub 14' to be changed, in a ratchet-like fashion, in discrete, 45° steps. As the relative rotational orientation changes (i.e., as knob 30' and hub 14' rotate with respect to one another), outermost points 212*a–h* move across flat surfaces 208*a–h*, initially forcing fingers 210*a–h* radially inward. When outermost points 212*a–h* move past the respective midpoints of the surfaces 208*a–h*, the elastic energy stored in the displaced flexible fingers 210*a–h* forces the fingers radially outward until relative rotational orientation between knob 30' and hub 14' has changed by 45°, and fingers 210*a–h* rest in the adjacent apex. Thus, fingers 210*a–h* positively urge outermost points 212*a–h* into each associated apex as it is encountered, thereby giving the surgeon kinesthetic feedback as to the amount by which distal tip 26 (FIG. 1)—and hence the surgical tool—has been bent, and helping to avoid accidental rotation of knob 30' with respect to hub 14'.

Of course, the ratcheting increments may be reduced from 45 degrees to any suitable amount by increasing the number of flat surfaces 208 and fingers 210 and correspondingly reducing their width.

Still other embodiments are within the scope of the claims.

What is claimed is:

1. A surgical instrument comprising
    a shaft disposed along a longitudinal axis between a proximal region and a distal region and including a flexible region therebetween, said shaft supporting a surgical tool at said distal region,
    a steering body connected to said shaft proximally of said surgical tool, said steering body having sufficient rigidity to transmit distally directed forces applied to a proximal end thereof to said shaft to bend said shaft in said flexible region and offset said surgical tool from said axis, and
    an actuator coupled to said proximal end of said steering body to apply said distally directed forces to said proximal end of said steering body.

2. The surgical instrument of claim 1 wherein said steering body is further constructed to transmit proximally directed forces applied to a proximal end thereof to said shaft to bend said shaft in said flexible region and offset said surgical tool from said axis, said actuator being coupled to apply said distally directed forces and said proximally directed forces to different portions of said proximal end of said steering body to bend said shaft.

3. A surgical instrument comprising
    a shaft disposed along a longitudinal axis between a proximal region and a distal region and including a flexible region therebetween, said shaft supporting a surgical tool at said distal region,
    a steering body connected to said shaft proximally of said surgical tool, said steering body having sufficient rigidity to transmit distally directed and proximally directed forces applied to a proximal end thereof to said shaft to bend said shaft in said flexible region and offset said surgical tool from said axis, said steering body comprising a plurality of generally rigid members disposed along said shaft, each of said members having a distal end connected to said shaft proximally of said surgical tool, and a flexible region disposed axially adjacent to said flexible region of said shaft, and
    an actuator coupled to proximal ends of said plurality of members of steering body to apply said distally directed and said proximally directed forces to said plurality of members to bend said shaft.

4. The surgical instrument of claim 3 wherein said actuator is coupled to a proximal end of each of said members for selectively moving said members in opposite proximal and distal directions along said axis, thereby to transmit said proximally directed and distally directed forces to said shaft.

5. The surgical instrument of claim 3 wherein said flexible region of said shaft terminates proximally of said opening, said members being connected to said shaft between said flexible region and said opening.

6. The surgical instrument of claim 3 wherein said members are semi-cylindrical sleeves which enclose said shaft.

7. The surgical instrument of claim 3 wherein each of said members is relieved with a plurality of openings to provide the flexible region thereof.

8. The surgical instrument of claim 7 wherein said openings comprise circumferentially extending slots disposed transversely to said axis in said members.

9. The surgical instrument of claim 8 wherein said slots are arranged to define a continuous strip of material that extends along a substantially straight line over an entire length of said flexible region of each of said members.

10. The surgical instrument of claim 3 further comprising a hub disposed at said proximal region of said shaft, said actuator including a knob mounted for relative rotation on said hub.

11. The surgical instrument of claim 10 wherein each of said members further comprises a transversely extending pin disposed at said proximal end, said knob including a plurality of channels configured to be engaged by said pins, said channels being oriented with respect to said longitudinal axis so that the engagement of said pins with said channels causes said members to move in opposite proximal and distal directions along said axis in response to relative rotation between said knob and said hub, thereby to transmit said proximally directed and distally directed forces to said shaft.

12. The surgical instrument of claim 11 wherein a pair of said channels are oriented in opposite inclined directions with respect to said longitudinal axis.

13. The surgical instrument of claim 12 wherein said pair of channels are helical.

14. The surgical instrument of claim 10 wherein said members further comprise second transversely extending pins disposed proximal of the first-mentioned pins, said hub including a plurality of passages configured to receive said second pins, said passages being oriented along said longitudinal axis so that the engagement of said second pins with said passages limits rotation of said proximal ends of said members in response to relative rotation between said knob and said hub.

15. The surgical instrument of claim 10 wherein said knob is mounted to said hub to allow continuous relative rotation therebetween.

16. The surgical instrument of claim 15 wherein said knob is mounted to said hub to allow relative rotation therebetween in discrete steps.

17. A surgical instrument comprising
an outer shaft disposed alone a longitudinal axis between a proximal region and a distal region and including a flexible region therebetween, said outer shaft supporting a surgical tool at said distal region,
an inner shaft movably disposed within said outer shaft and having a flexible region positioned axially adjacent to said flexible region of said outer shaft,
said surgical tool comprising an opening in said distal region of said outer shaft and an implement carried by said inner shaft for cutting tissue exposed thereto through said opening,
a steering body connected to said outer shaft proximally of said surgical tool, said steering body having sufficient rigidity to transmit distally directed forces applied to a proximal end thereof to said outer shaft to bend said outer shaft in said flexible region and offset said surgical tool from said axis, and
an actuator coupled to said proximal end of said steering body to apply said distally directed forces to said proximal end of said steering body.

18. The surgical instrument of claim 17 wherein said implement includes a sharpened edge at said distal end of said inner shaft.

19. A surgical instrument comprising
a shaft disposed along a longitudinal axis between a proximal region and a distal region and including a flexible region therebetween, said shaft supporting a surgical tool at said distal region,
a steering body comprising a plurality of generally rigid members disposed along said shaft, each of said members having a distal end connected to said shaft proximally of said surgical tool, and a flexible region disposed axially adjacent to said flexible region of said shaft, each of said members having sufficient rigidity to transmit proximally directed and distally directed forces applied to a proximal end thereof to said shaft to bend said shaft in said flexible region and offset said surgical tool from said axis,
a hub which receives proximal ends of said members and said proximal region of said shaft, and
an actuator mounted for relative rotation with respect to said hub, said actuator being coupled to a proximal end of each of said members for selectively moving said members in opposite proximal and distal directions along said axis to transmit said proximally directed forces to said distal end of said shaft with one of said members and transmit said distally directed forces to said shaft with another one of said members, thereby to bend said shaft in said flexible region and offset said surgical tool from said axis.

20. A surgical instrument for removing tissue from a body comprising
a steering body comprising a pair of generally rigid, semi-cylindrical members each of which includes a proximal end, a distal end, an intermediate flexible region, and a pin extending from said proximal end transversely to said axis,
a generally rigid outer tubular shaft including a proximal end, a distal end, an intermediate flexible region, and an opening in said distal end of said outer shaft for admitting tissue, said semi-cylindrical members being disposed on said outer shaft with the flexible regions thereof in alignment and the distal ends of said semi-cylindrical members being secured to said outer shaft proximally adjacent to said opening,
a generally rigid inner tubular shaft including a proximal end, a distal end, an intermediate flexible region, and a cutting implement disposed at said distal end of said inner shaft for cutting tissue admitted through said opening, said inner shaft being disposed within said outer tubular shaft with the flexible regions thereof in alignment,
each of said members having sufficient rigidity to transmit proximally directed and distally directed forces applied to a proximal end thereof to said outer tubular shaft to bend said outer tubular shaft at its intermediate flexible region and said inner tubular shaft at its intermediate flexible region,
a hub which receives the proximal ends of said members, said outer tubular shaft, and said inner tubular shaft, and
a knob mounted for relative rotation with respect to said hub, said knob including a pair of helical channels within which said pins are disposed, said channels being oriented with respect to said longitudinal axis so that the engagement of said plus with said channels cause said members to move in opposite proximal and distal direction along said axis in response to relative rotation to respectively transmit said proximally directed and distally directed forces to said outer tubular shaft to bend said steering body, said outer tubular shaft, and said inner tubular shaft in the flexible region thereof and offset said surgical tool from said axis.

21. The surgical instrument of claim 20 wherein said members, said outer tubular shaft, and said inner tubular shaft are each relieved with a plurality of openings to provide the flexible region thereof.

22. The surgical instrument of claim 20 wherein said members further comprise second transversely extending pins disposed proximal of the first-mentioned pins, said hub including a plurality of passages configured to receive said second pins, said passages being oriented along said longitudinal axis so that the engagement of said second pins with said passages limits rotation of said proximal ends of said members in response to relative rotation between said knob and said hub.

23. The surgical instrument of claim 20 further comprising a sheath disposed over at least said flexible region of said inner tubular shaft.

24. The surgical instrument of claim 20 further comprising a sheath disposed over said members between said hub and said distal ends of said members.

25. A surgical method comprising providing a surgical instrument that includes
- a shaft disposed along a longitudinal axis between a proximal region and a distal region and including a flexible region therebetween, said shaft supporting a surgical tool at said distal region,
- a steering body connected to said shaft proximally of said surgical tool, said steering body having sufficient rigidity to transmit distally directed forces applied to a proximal end thereof to said shaft to bend said shaft in said flexible region and offset said surgical tool from said axis, and
- an actuator coupled to said proximal end of said steering body to apply said distally directed forces to said proximal end of said steering body;

directing said surgical instrument to place said surgical tool in a first position with respect to body tissue; and manipulating said actuator to cause said steering body to apply said distally directed forces to said shaft to bend said shaft and offset said surgical tool from said axis to place said surgical tool in a second, different position with respect to the body tissue.

26. The method of claim 25 wherein said steering body is further constructed to transmit proximally directed forces applied to a proximal end thereof to said shaft to bend said shaft in said flexible region and offset said surgical tool from said axis, said actuator being coupled to apply said distally directed forces and said proximally directed forces to different portions of said proximal end of said steering body to bend said shaft, and further comprising manipulating said actuator to apply said distally directed forces and said proximally directed forces to said different portions to bend said shaft and offset said surgical tool from said axis to place said surgical tool in the second position.

* * * * *

UNITED STATES PATENT AND TRADEMARK OFFICE
CERTIFICATE OF CORRECTION

PATENT NO.   : 5,921,956

DATED        : July 13, 1999

INVENTOR(S)  : Alexander Grinberg et al.

It is certified that error appears in the above-identified patent and that said Letters Patent is hereby corrected as shown below:

Col. 11, claim 17, line 37, replace "alone" with --along--.

Col. 12, claim 20, line 56, replace "plus" with --pins--;
line 57, replace "cause" with --causes--;
line 58, replace "direction" with --directions--;
line 59, after "rotation" insert --between said knob and said hub, thereby causing said members--;
line 62, replace "region" with --regions--.

Signed and Sealed this

Seventh Day of March, 2000

Attest:

Q. TODD DICKINSON

Attesting Officer

Commissioner of Patents and Trademarks